(12) United States Patent
DeNatale et al.

(10) Patent No.: US 7,329,932 B2
(45) Date of Patent: Feb. 12, 2008

(54) MICROELECTROMECHANICAL (MEM) VISCOSITY SENSOR AND METHOD

(75) Inventors: Jeffrey F. DeNatale, Thousand Oaks, CA (US); Robert L. Borwick, III, Thousand Oaks, CA (US); Philip A. Stupar, Oxnard, CA (US)

(73) Assignee: Teledyne Licensing, LLC, Thousand Oaks, CA (US)

( * ) Notice: Subject to any disclaimer, the term of this patent is extended or adjusted under 35 U.S.C. 154(b) by 173 days.

(21) Appl. No.: 11/224,798

(22) Filed: Sep. 12, 2005

(65) Prior Publication Data

US 2007/0057336 A1   Mar. 15, 2007

(51) Int. Cl.
*H01L 29/84* (2006.01)
*H01L 21/00* (2006.01)

(52) U.S. Cl. .................... 257/417; 438/51; 438/53
(58) Field of Classification Search ............ None
See application file for complete search history.

(56) References Cited

U.S. PATENT DOCUMENTS

| 4,926,682 A | 5/1990 | Holm-Kennedy et al. ..... 73/54 |
| 4,975,390 A | 12/1990 | Fujii et al. ............. 437/228 |
| 5,025,346 A | 6/1991 | Tang et al. ............. 361/283 |
| 5,199,298 A | 4/1993 | Ng et al. ............... 73/54.01 |
| 5,295,395 A | 3/1994 | Hocker et al. ............ 73/721 |
| 5,798,283 A | 8/1998 | Montague et al. ........... 438/24 |
| 6,042,682 A | 3/2000 | Funaya et al. ........... 156/273.3 |
| 6,159,385 A | 12/2000 | Yao et al. ................. 216/2 |
| 6,769,319 B2 | 8/2004 | McDonald et al. ........ 73/866.1 |
| 2002/0197002 A1 | 12/2002 | Lin |
| 2004/0027029 A1 | 2/2004 | Borwick, III et al. |
| 2004/0077119 A1 | 4/2004 | Ikeda et al. |
| 2004/0113513 A1 | 6/2004 | Borwick, III et al. |

OTHER PUBLICATIONS

PCT International Search Report; Aug. 15, 2007; in International Application No. PCT/US06/35494; 2 pps.
PCT Written Opinion of the International Searching Authority; Aug. 15, 2007; in International Application No. PCT/US06/35494; 7 pps.

*Primary Examiner*—Alonzo Chambliss
(74) *Attorney, Agent, or Firm*—Koppel, Patrick, Heybl & Dawson

(57) ABSTRACT

A MEM viscosity sensor comprises a substrate, with first and second support structures affixed to the substrate and spaced-apart. A compliant member is affixed to the support structures such that it is suspended above and can flex vertically with respect to the substrate. The member has a high density of perforations, through which a fluid whose viscosity is to be sensed can flow. The sensor includes a drive means to apply a force to the member, and a sensing means to sense the vertical motion of the member in response to the applied force. The member's perforations ensure that its resistance to motion will be shear in nature, and minimizes sensitivity to particulates. The substrate is also preferably perforated to further reduce non-shear forces and facilitate fluid exchange.

43 Claims, 4 Drawing Sheets

SECTION A-A

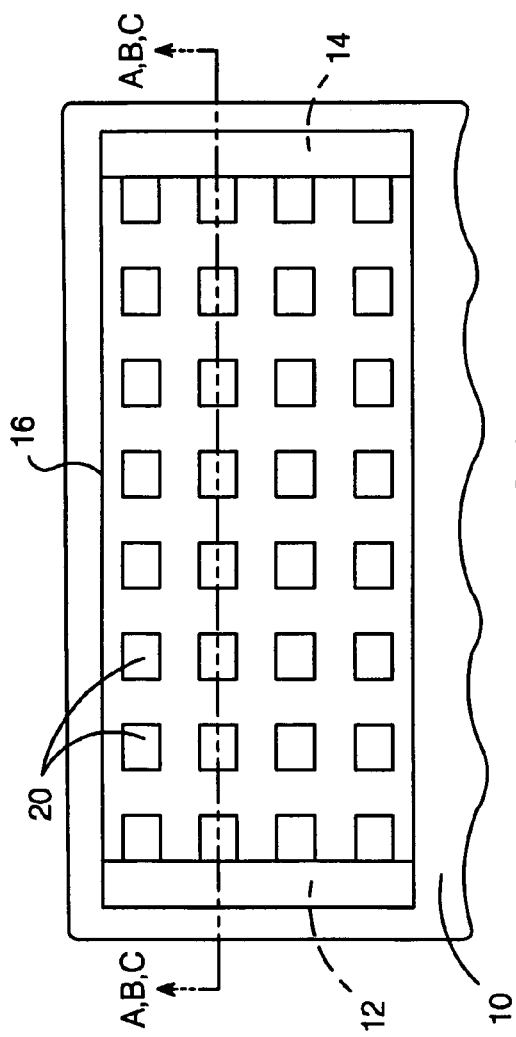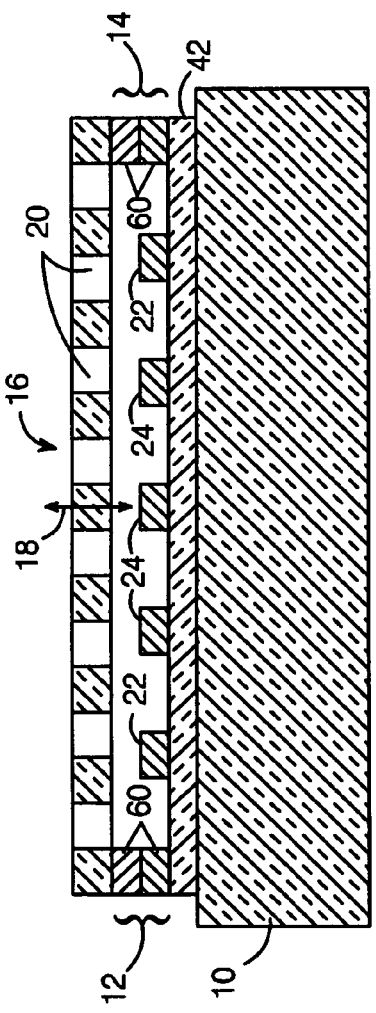

SECTION B-B

SECTION C-C

MICROELECTROMECHANICAL (MEM) VISCOSITY SENSOR AND METHOD

BACKGROUND OF THE INVENTION

1. Field of the Invention

This invention relates to the field of viscosity sensors, and particularly to viscosity sensors made from micromechanical (MEM) devices.

2. Description of the Related Art

Many mechanical systems require fluids for their operation. Extending the life of such systems requires that such fluids must be maintained, including the replacement of spent and degraded liquids. One method of assessing the health of such a fluid is to measure its viscosity.

Many devices have been developed to measure viscosity. One approach uses a vibrating quartz or piezoelectric element that measures the shift in a device's resonant frequencies or change in quality factor, Q, in response to applied vibrations; the frequency shift is a measurement of the damping value, which varies with viscosity. The measurement of damping value, however, is not a linear measurement, and thus will not be useful over a wide viscosity range. Further, this manner of measuring viscosity introduces complexities because both compressive and shear forces are applied to the sensing element; the contributions of both components to the net response can complicate data interpretation and limit operating range.

Microelectromechanical (MEM) devices—i.e., integrated devices which include at least one moveable element that moves relative to a stationary element—have also been employed to measure viscosity; MEM-based viscosity sensors are described, for example, in co-pending patent application Ser. Nos. 10/956,229 and 11/222,721 and assigned to the same assignee as the present application. In operation, the sensor is immersed in the fluid being assessed, the moveable element is commanded to move through the fluid, and the time it takes to respond is measured. The time response varies with the fluid's viscosity.

These devices use lateral motion in a fluid to generate the sort of nearly pure shear response required for accurate viscosity measurements. Movable and stationary interdigitated comb structures are moved laterally with respect to each other, with the resulting capacitance varying with the amount of overlap between the structures. However, due to the close proximity of the movable and stationary comb structures, this type of device may be particularly sensitive to particulate contamination.

SUMMARY OF THE INVENTION

A MEM viscosity sensor and method are presented which overcome the problems noted above, providing accurate viscosity measurements while being largely insensitive to particulate contamination.

A MEM viscosity sensor per the present invention comprises a substrate, with first and second support structures affixed to the substrate and spaced-apart. A compliant member having first and second ends is affixed to the first and second support structures, respectively, such that the member is suspended above the substrate and can flex vertically with respect to the substrate. The compliant member has a high density of perforations, through which a fluid whose viscosity is to be sensed can flow. The sensor also includes a drive means arranged to apply a force to the compliant member such that it moves vertically with respect to the substrate, and a sensing means arranged to sense the motion of the member in response to the applied force.

In operation, the drive means causes the compliant member—typically a thin plate—to move vertically with respect to the substrate. Due to the member's high density of perforations, its resistance to motion will be nearly entirely shear in nature, avoiding measurement complications that might otherwise arise due to normal forces and fluid inertial effects; the perforations also reduce sensitivity to particulates relative to interdigitated comb devices. The time response of the member is sensed, from which the viscosity of the fluid can be determined.

The portion of the substrate beneath the compliant member preferably has a high density of perforations as well. This enables the fluid to flow through the substrate portion via the perforations, further reducing non-shear forces on the compliant member and facilitating fluid exchange.

Further features and advantages of the invention will be apparent to those skilled in the art from the following detailed description, taken together with the accompanying drawings.

BRIEF DESCRIPTION OF THE DRAWINGS

FIG. 1 is a plan view of a MEM viscosity sensor in accordance with the present invention.

FIG. 2 is a cross-sectional view of the MEM viscosity sensor of FIG. 1, cut along section line A-A.

DETAILED DESCRIPTION OF THE INVENTION

Figure 3:
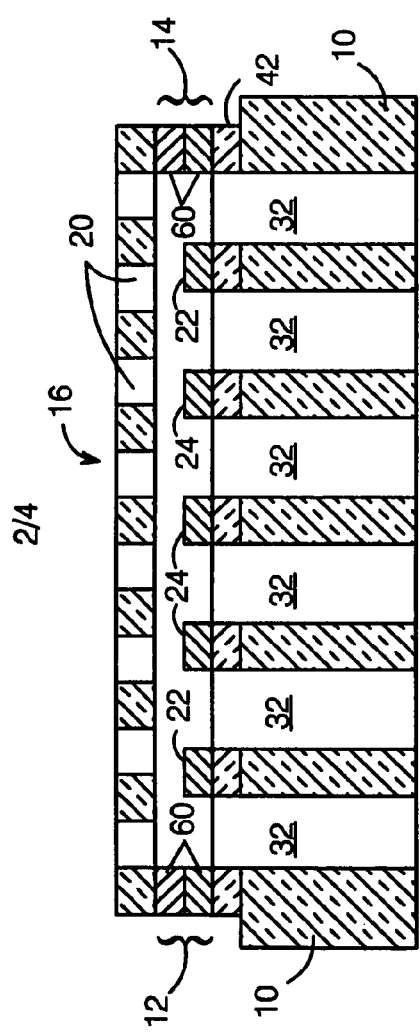
FIG. 3 is a cross-sectional view of the MEM viscosity sensor of FIG. 1 for a device implementation incorporating substrate perforations, cut along section line B-B.

The present invention is directed to a MEM viscosity sensor and method which provide accurate viscosity measurements while being less sensitive to particulate contamination relative to prior art sensors using interdigitated comb capacitors.

A plan view of a sensor in accordance with the present invention is shown in FIG. 1, with one possible cross-sectional view, cut along section line A-A, shown in FIG. 2. A substrate 10 is provided, and first and second spaced-apart support structures 12, 14 are affixed atop the substrate. A compliant member 16 has first and second ends, which are affixed to the first and second support structures, respectively, such that compliant member 16 is suspended between support structures 12, 14 and above substrate 10, and can flex vertically 18 with respect to the substrate. Compliant member 16 has a high density of fine-scale perforations 20, through which a fluid whose viscosity is to be sensed can flow.

The MEM viscosity sensor also requires a drive means 22 arranged to apply a force to compliant member 16 such that it moves vertically with respect to substrate 10, and a sensing means 24 arranged to sense the motion of the member in response to the applied force.

The perforations in compliant member 16 tend to reduce compressive forces on the member. Therefore, when the sensor is immersed in a fluid whose viscosity is to be sensed, the member's resistance to motion when moving through the fluid will be nearly entirely shear in nature, as required for an accurate determination of viscosity. Perforations 20 also reduce sensitivity to particulate contamination relative to interdigitated comb devices, and reduce the chance of impeded motion.

In operation, drive means 22 causes compliant member 16—typically a thin plate—to move vertically with respect to substrate 10. The time response of the member is sensed, from which the viscosity of the fluid can be determined.

Drive means 22 is preferably an electrostatic actuator; voltages are applied between compliant member 16 and one or more electrodes on substrate 10 to generate an electrostatic force which attracts compliant member 16 towards the substrate. Other actuator types might also be employed, including thermal, electromagnetic, Lorentz force, or piezoelectric actuators. Additional details about various drive means are described, for example, in U.S. Pat. No. 5,025,346 (electrostatic), and U.S. Patent Publication US 2004/0027029 (Lorentz). Electrical isolation between actuator elements can be achieved using dielectric layers on the substrate and/or compliant member.

Sensing means 24 preferably employs capacitive sensing. The capacitance present between one or more electrodes on substrate 10 and compliant member 16 is sensed as member 16 moves in response to the applied force. External circuitry monitors the varying capacitance to determine the time response of the member, and thereby the viscosity of the fluid in which it is immersed. Alternate sensing methods might also be employed, including piezoresistive or optical interference methods.

Compliant member 16 could be configured in any of a number of ways. A preferred embodiment is that of a thin compliant plate, having a thickness of 20-50 µm. The member could be fabricated from a number of different materials, including, for example, silicon, nickel, aluminum or titanium. Single crystal silicon is preferred.

The portion of substrate 10 beneath compliant member 16 may also be perforated; a cross-sectional view of this possible implementation, cut along section line B-B of FIG. 1, is shown in FIG. 3. The sensor is similar to that shown in FIG. 2, except that substrate 10 has a high density of perforations 32 in at least the area beneath member 16. These perforations tend to further reduce compressive, non-shear forces on member 16, and to facilitate fluid exchange. The perforations in substrate 30 are preferably larger than those in compliant member 16.

Figure 4:
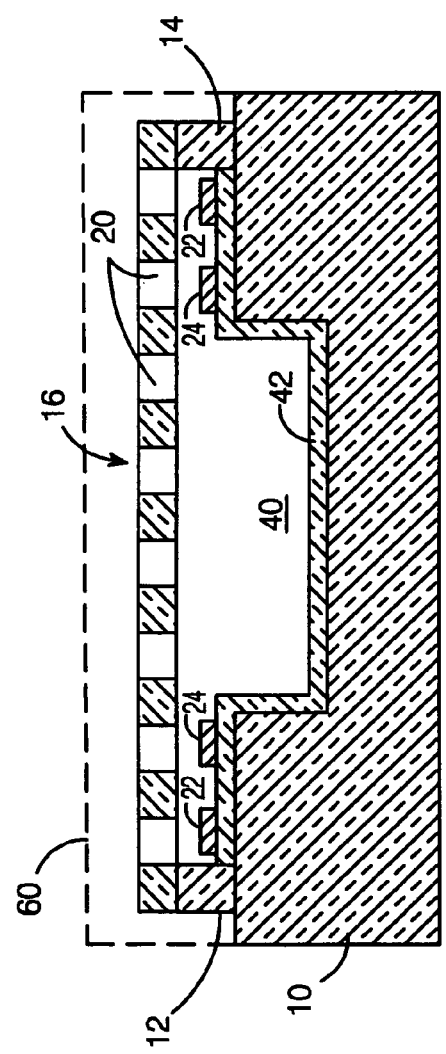
FIG. 4 is a cross-sectional view of the MEM viscosity sensor of FIG. 1 for a device implementation incorporating a substrate recess, cut along section line C-C.

A cross-sectional view of another possible implementation, cut along section line C-C of FIG. 1, is shown in FIG. 4. Here, instead of perforations in substrate 10, a recessed area 40 is etched into substrate 10 in the area beneath compliant member 16, to facilitate fluid flow through the compliant member.

Note that a viscosity sensor per the present invention might also include one or more insulating layers which provide electrical isolation. For example, if drive means 22 is an electrostatic actuator, a voltage differential must be applied between member 16 and substrate 10, which generates an electrostatic force that causes deflection of the compliant member. If member 16 and substrate 10 are fabricated such that they would be electrically continuous in the absence of an insulating layer, a voltage differential could not be sustained. An insulating layer for this purpose could be employed in a number of places, such as between substrate 10 and support structures 12 and 14, between the support structures and compliant member 16, or under the drive electrodes on substrate 10.

An insulating layer may also be important to the sensor's sensing means. If both the drive electrodes and the sensing electrodes are located on a non-insulating substrate 10, a means of electrically isolating the electrodes from each other is needed to permit capacitive sensing and eliminate coupling between the two.

Possible sensor implementations which include an insulating layer are shown in FIGS. 2-4, in which an insulating layer 42 is deposited on substrate 10, with drive electrodes 22 and sense electrodes 24 formed on top of layer 42. To deflect member 16, a voltage differential would be applied between the drive electrodes and a contact electrically continuous to compliant member 16.

To ensure that the compliant member and the stationary substrate and/or substrate contacts are not shorted together when the member is pulled down, an insulating layer can be employed on the bottom surface of member 16 (facing the substrate), or by incorporating insulating standoffs that prevent member 16 from physically contacting the substrate or substrate electrodes.

If it is preferred to have substrate 10 as a common ground, and to actuate the sensor by applying a voltage to compliant member 16, an insulating layer may need to be on the bottom surface of member 16. If capacitive sensing is employed, the capacitive sense electrodes would need to be located on the bottom surface of member 16 along with the drive electrodes, and the insulating layer would be used to isolate the electrodes from each other.

The insulating layer could be deposited as a thin film, or by thermal oxidation, or by a number of other deposition techniques for insulating films known to those skilled in the art.

Figure 5:
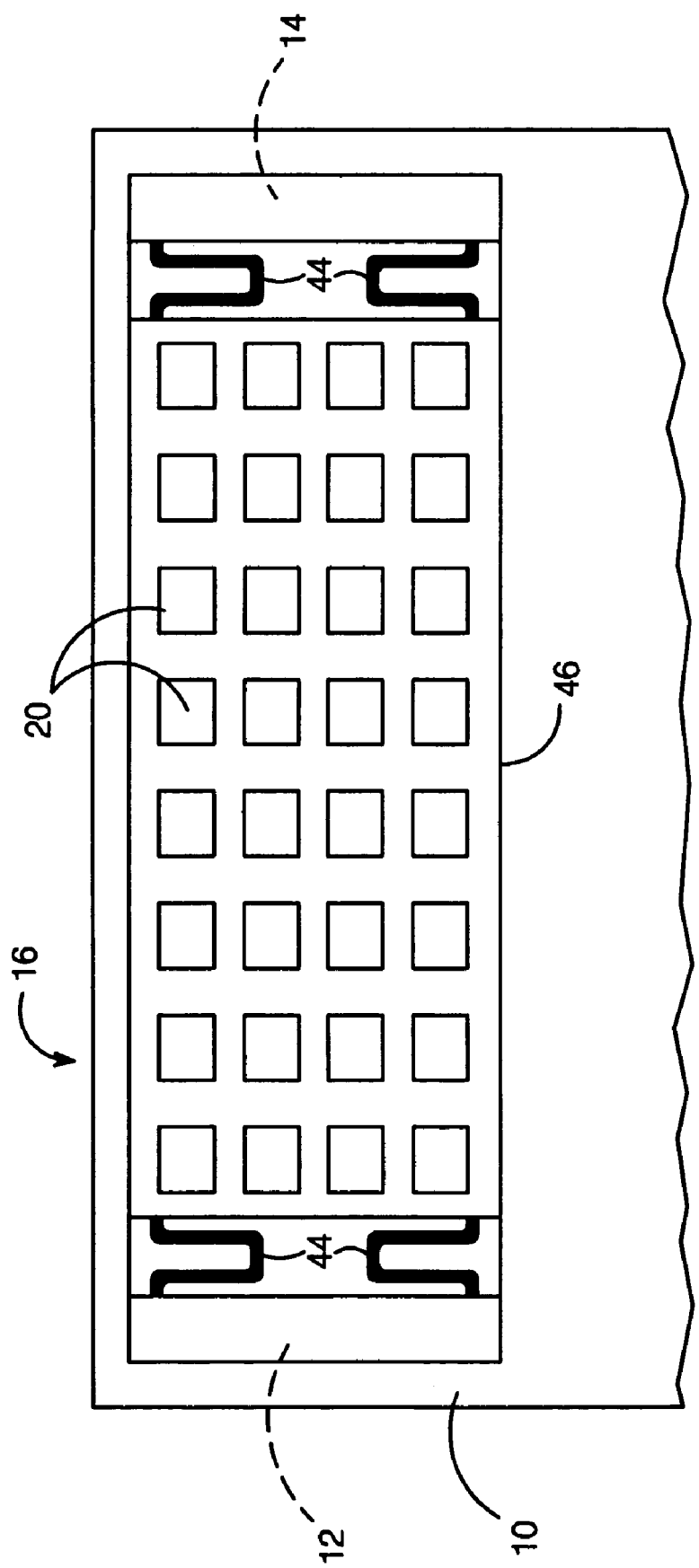
FIG. 5 is a plan view of an alternative embodiment of a compliant member as might be used with the present invention.

As noted above, compliant member 16 could be configured in a number of ways; a plan view of one possible alternative arrangement is shown in FIG. 5. Here, member 16 comprises compliant mechanical flexures 44 and a rigid perforated plate 46. The compliance of the flexures and plate may be designed to achieve the desired mechanical characteristics and actuation behavior.

A viscosity sensor in accordance with the present invention is preferably operated by causing drive means 22 to apply force to member 16 as a step input. The sensor is preferably arranged to operate in an overdamped mode in response to the step input, which provides a wider measurement range than would a sensor tuned to operate in an underdamped mode. The sensor's mechanical response can be tuned by, for example, adjusting the mass and the stiffness of compliant member 16, and/or using separate flexures between member 16 and support structures 12 and 14.

Figure 6:
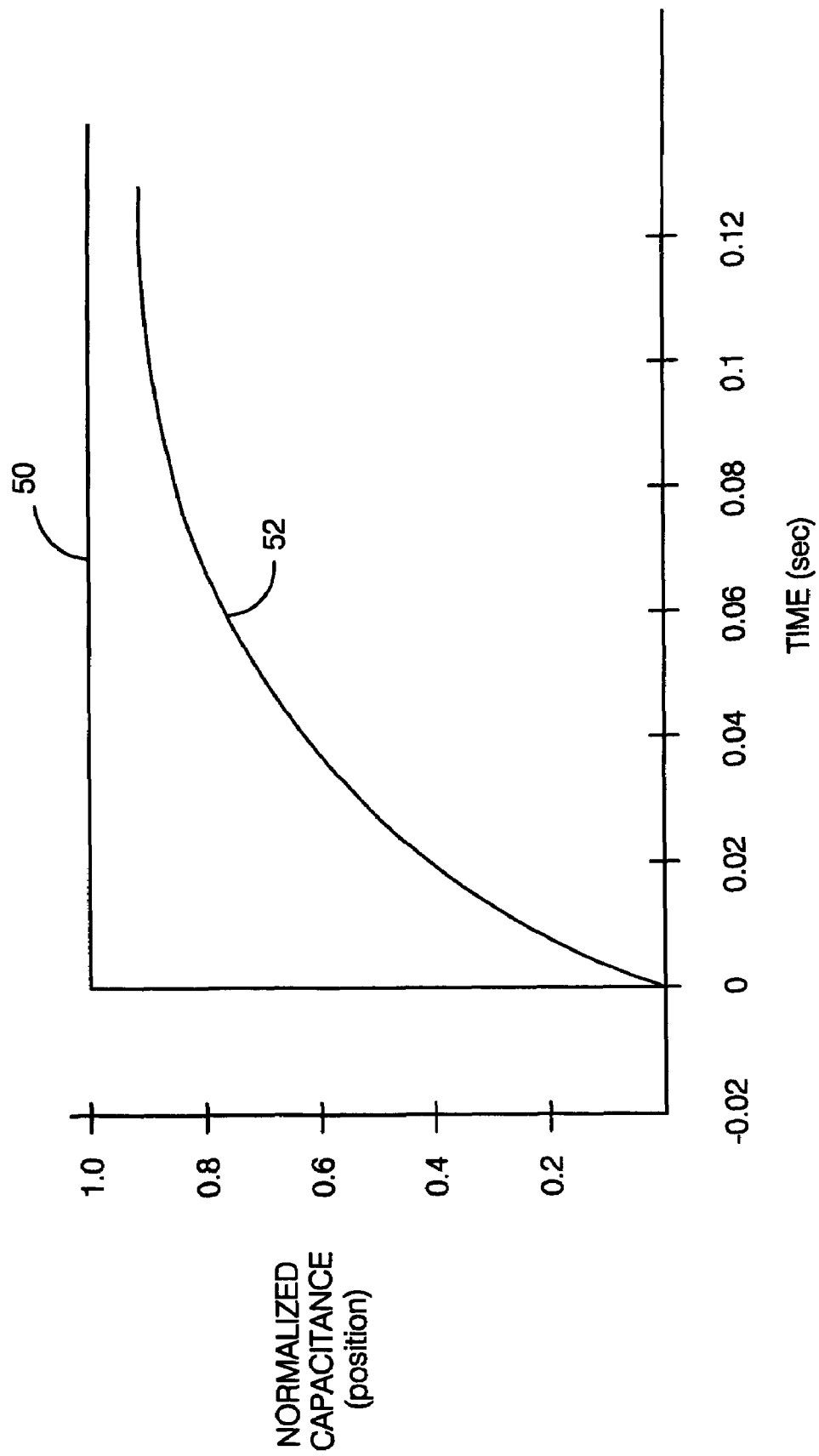
FIG. 6 is a plot of normalized capacitance vs. time for a MEM viscosity sensor in accordance with the present invention.

Operation of the sensor is illustrated in FIG. 6, which depicts an ideal step function 50 representing the applied force, and the resulting time response (52) of capacitance (assuming that capacitive sensing is being employed), which is a function of position. In response to a step function input, the overdamped system asymptotically displaces to a maximum value, which is normalized to 1. Assuming that the relationship between fluid viscosity and time response have been previously determined, the viscosity of the fluid being tested is derived from the measured time response. The health of the fluid can be determined by comparing the measured value of viscosity with the healthy viscosity value for the fluid being tested.

Referring back to FIG. 4, a sensor per the present invention might be enclosed within a housing 60 which includes a perforated portion (not shown) through which the fluid to be tested can flow. This perforated portion can serve to filter the fluid in which the sensor is immersed.

A MEM viscosity sensor per the present invention is preferably fabricated using a semiconductor wafer—preferably a silicon-on-insulator (SOI) wafer, and a substrate—which can be insulating or conductive. The sensor's first and second support structures are formed on the substrate. The wafer is then bonded to the substrate to form a composite structure. Portions of the composite structure are patterned and etched to form the perforated compliant member, the drive means and the sensing means. A deep reactive ion etch (DRIE) process is preferably used to etch the SOI wafer's device layer.

The wafer can be bonded to the substrate using, for example, an organic adhesive. Alternatively, as illustrated in FIGS. 2 and 3, respective bonding pads 60 can be fabricated on the wafer and substrate, which are aligned and mechanically connected to form a thermocompression bond which effects the bonding; here, the bonding pads form support structures 12 and 14. For the latter case, the bonding pads are preferably gold (Au), such that the thermocompression bond is an Au—Au thermocompression bond. The wafer and substrate might also be bonded using anodic bonding, fusion bonding, or solder bonding, or other processes known to those skilled in the art.

One or more metallization layers would typically be deposited on the composite structure and patterned through etching or liftoff methods to provide electrical interconnections for the sensor. The metallization might be aluminum-based, gold-based, or alternatively, comprise a conductive refractory material. Note that additional circuitry may be fabricated directly on the wafer or substrate before, during, or after the MEM fabrication process. Additional details about the preferred fabrication methods are described, for example, in U.S. Pat. No. 6,159,385, U.S. Patent Publication US 2004/0113513, and co-pending patent application Ser. No. 11/222,721, which are assigned to the same assignee as the present case and are incorporated herein by reference.

Embodiments of a viscosity sensor as described herein can be utilized in a variety of situations in which measurements determining the health of a liquid are desired. For example, the present sensor can be installed in the oil tank of a vehicle, machine, or in a separate testing apparatus to which liquid samples are brought. The sensors could be used for in-situ fluid health monitoring, immersed, for example, in the working fluids of pumps, turbines, engines, etc. They might also be advantageously employed in fluid processing applications, such as in the chemical or food processing industries, where chemical inertness is critical.

While particular embodiments of the invention have been shown and described, numerous variations and alternate embodiments will occur to those skilled in the art. Accordingly, it is intended that the invention be limited only in terms of the appended claims.

We claim:

1. A microelectromechanical (MEM) viscosity sensor, comprising:
a substrate;
first and second support structures on said substrate, said support structures spaced-apart;
a compliant member having first and second ends, said first and second ends affixed to said first and second support structures, respectively, such that said member is suspended between said support structures and above said substrate and can flex vertically with respect to said substrate, said member having a high density of perforations through which a fluid whose viscosity is to be sensed can flow;
a drive means coupled to said compliant member and arranged to apply a force to said member such that said member moves vertically with respect to said substrate; and
a sensing means coupled to said compliant member and arranged to sense the motion of said member in response to said force.

2. The sensor of claim 1, wherein said sensor is arranged such that said compliant member is subjected to a predominately shear force when moving through said fluid.

3. The sensor of claim 1, wherein said drive means is selected from a group consisting of an electrostatic actuator, thermal actuator, electromagnetic actuator, Lorentz force actuator, or piezoelectric actuator.

4. The sensor of claim 1, wherein said sensing means is arranged to provide an output which varies with the position between said compliant member and said substrate based on said sensing means.

5. The sensor of claim 1, wherein said sensing means is arranged to provide an output which varies with the position of the compliant member based on piezoresistive or optical sensing methods.

6. The sensor of claim 1, wherein said compliant member is a plate having a thickness of 20-50 μm.

7. The sensor of claim 1, wherein said compliant member comprises single crystal silicon.

8. The sensor of claim 1, wherein the portion of said substrate beneath said compliant member has a high density of perforations such that said fluid can flow through said substrate portion via said perforations.

9. The sensor of claim 8, wherein the perforations in said substrate portion are larger than those in said compliant member.

10. The sensor of claim 1, wherein the portion of said substrate beneath said compliant member comprises a recessed area to facilitate fluid flow through said compliant member.

11. The sensor of claim 1, wherein said drive means is arranged to apply said force as a step input.

12. The sensor of claim 1, wherein said sensor is arranged to operate in an overdamped mode when said force is applied to said compliant member.

13. The sensor of claim 1, further comprising a housing which encapsulates said substrate, support structures, compliant member, drive means and sensing means, said housing including a perforated portion through which said fluid can flow.

14. The sensor of claim 1, wherein said complaint member comprises:
a rigid perforated plate; and
compliant mechanical flexures coupled between said plate and said support structures such that said plate is suspended between said support structures via said compliant mechanical flexures.

15. The sensor of claim 1, further comprising an insulating layer arranged to enable a voltage differential to be applied between said substrate and said compliant member.

16. The sensor of claim 1, further comprising an insulating layer arranged to electrically isolate said substrate from said compliant member.

17. The sensor of claim 1, wherein said drive means comprises one or more electrodes on said substrate, further comprising an insulating layer arranged to electrically isolate said electrodes from said substrate.

18. The sensor of claim 17, wherein said sensing means comprises one or more electrodes on said substrate and said insulating layer is arranged to electrically isolate said drive electrodes from said sensing electrodes.

19. The sensor of claim 1, further comprising an insulating means which prevents electrical contact between said compliant member and said substrate and/or electrodes on said substrate.

20. The sensor of claim 19, wherein said insulating means comprises an insulating layer affixed to the substrate side of said compliant member.

21. The sensor of claim 19, wherein said insulating means comprises insulating standoffs.

22. A microelectromechanical (MEM) viscosity sensor, comprising:
   a substrate;
   first and second support structures on said substrate, said support structures spaced-apart;
   a compliant member having first and second ends, said first and second ends affixed to said first and second support structures, respectively, such that said member is suspended between said support structures and above said substrate and can flex vertically with respect to said substrate, said member and the portion of said substrate beneath said member each having a high density of perforations through which a fluid whose viscosity is to be sensed can flow and such that said compliant member is subjected to a predominately shear force when moving through said fluid;
   an electrostatic drive means coupled to said compliant member and arranged to apply a force to said member such that said member moves vertically with respect to said substrate; and
   a capacitive sensing means coupled to said compliant member and arranged to sense the motion of said member in response to said force.

23. The sensor of claim 22, wherein said drive means is arranged to apply said force as a step input and said sensor is arranged to operate in an overdamped mode in response to said step input.

24. A microelectromechanical (MEM) viscosity sensor, comprising:
   a semiconductor wafer; and
   a substrate bonded to said wafer and thereby forming a composite structure, portions of said composite structure patterned and etched to form:
      first and second support structures on said substrate, said support structures spaced-apart; and
      a compliant member having first and second ends, said first and second ends affixed to said first and second support structures, respectively, such that said member is suspended between said support structures and above said substrate and can flex vertically with respect to said substrate, said member having a high density of perforations through which a fluid whose viscosity is to be sensed can flow;
   a drive means coupled to said compliant member and for displacing said compliant member vertically relative to said substrate; and
   a sensing means coupled to said compliant member and arranged to sense the motion of said member in response to said force.

25. The sensor of claim 24, further comprising an organic adhesive which bonds said substrate to said wafer.

26. The sensor of claim 24, wherein said wafer and substrate have respective bonding pads which are aligned and mechanically connected such that a thermocompression bond is formed to effect the bonding of said wafer to said substrate.

27. The sensor of claim 26, wherein said bonding pads are gold (Au) and said thermocompression bond is an Au—Au thermocompression bond.

28. The sensor of claim 24, wherein said wafer and substrate have respective bonding regions which are aligned and mechanically connected such that an anodic bond is formed to effect the bonding of said wafer to said substrate.

29. The sensor of claim 24, wherein said wafer is a silicon-on-insulator (SOI) wafer.

30. The sensor of claim 24, wherein said substrate is a semiconductor wafer containing additional circuitry.

31. The sensor of claim 24, further comprising one or more metallization layers deposited on said composite structure and patterned through etching or liftoff methods to provide electrical interconnections for said sensor.

32. The sensor of claim 31, wherein said metallization layers comprise a conductive refractory material.

33. A method of measuring the viscosity of a fluid, comprising:
   providing a microelectromechanical (MEM) viscosity sensor, comprising:
      a substrate;
      first and second support structures on said substrate, said support structures spaced-apart;
      a compliant member having first and second ends, said first and second ends affixed to said first and second support structures, respectively, such that said member is suspended between said support structures and above said substrate and can flex vertically with respect to said substrate, said member having a high density of perforations through which a fluid whose viscosity is to be sensed can flow;
      a drive means coupled to said compliant member and arranged to apply a force to said member such that said member moves vertically with respect to said substrate; and
      a sensing means coupled to said compliant member and arranged to sense the motion of said member in response to said force;
   immersing said sensor in said fluid;
   operating said drive means such that said force is applied to said compliant member as a step input; and
   measuring the time response of said compliant member using said sensing means.

34. The method of claim 33, wherein the portion of said substrate beneath said compliant member has a high density of perforations such that said fluid can flow through said substrate portion via said perforations.

35. The method of claim 33, wherein said sensor is arranged to operate in an overdamped mode when said force is applied to said compliant member.

36. A method of fabricating a microelectromechanical (MEM) viscosity sensor, comprising:
   providing a semiconductor wafer;
   providing a substrate;
   forming first and second support structures on said substrate, said support structures spaced-apart; and
   bonding said wafer and substrate together to form a composite structure; and
   patterning and etching portions of said composite structure to form a compliant member having first and second ends, said first and second ends affixed to said first and second support structures, respectively, such that said member is suspended between said support structures and above said substrate and can flex vertically with respect to said substrate, said member having a high density of perforations through which a fluid whose viscosity is to be sensed can flow.

37. The method of claim 36, further comprising patterning and etching said substrate to provide a high density of perforations through said substrate such that said fluid can flow through said substrate via said perforations.

38. The method of claim 36, further comprising:
patterning and etching a recessed area into said substrate beneath said compliant member to facilitate fluid flow through said compliant member.

39. The method of claim 36, wherein said bonding comprises:
patterning one or more bonding pads on said wafer;
patterning one or more bonding pads on said substrate such that said substrate's bonding pads can be aligned with said wafer's bonding pads;
aligning said wafer's bonding pads with said substrate's bonding pads; and
mechanically connecting the bonding pads of said wafer and substrate to produce a thermocompression bond which bonds said wafer and substrate.

40. The method of claim 39, wherein said bonding pads are gold bonding pads and said thermocompression bond is an Au—Au thermocompression bond.

41. The method of claim 36, further comprising depositing one or more metallization layers on said composite structure and patterning through etching or liftoff methods to provide electrical interconnections for said sensor.

42. The method of claim 41, wherein said metallization layers comprise a conductive refractory material.

43. The method of claim 36, further comprising depositing an insulating layer between said substrate and said compliant member.

* * * * *